United States Patent [19]
Andersen

[11] Patent Number: 5,840,169
[45] Date of Patent: *Nov. 24, 1998

[54] APPARATUS AND PROCESS FOR ELECTROELUTION OF A GEL CONTAINING CHARGED MACROMOLECULES

[76] Inventor: Peter Andersen, Lystrupvej 7, DK-2700 Bronshoj, Denmark

[*] Notice: The portion of the term of this patent subsequent to Aug. 13, 2011, has been disclaimed.

[21] Appl. No.: 290,993

[22] PCT Filed: Feb. 25, 1992

[86] PCT No.: PCT/DK92/00058

§ 371 Date: Mar. 13, 1995

§ 102(e) Date: Mar. 13, 1995

[87] PCT Pub. No.: WO93/16788

PCT Pub. Date: Sep. 2, 1993

[51] Int. Cl.[6] ................................................. G01N 27/26
[52] U.S. Cl. ........................ 204/462; 204/464; 204/613; 204/614
[58] Field of Search ........................... 204/182.8, 299 R, 204/180.1, 462, 464, 613, 614

[56] References Cited

U.S. PATENT DOCUMENTS

| | | |
|---|---|---|
| 3,956,099 | 5/1976 | Israel et al. . |
| 4,049,534 | 9/1977 | Posner . |
| 4,181,594 | 1/1980 | Rizk et al. . |
| 4,608,147 | 8/1986 | Clad ........................................ 204/301 |
| 4,725,348 | 2/1988 | Diekmann . |
| 4,747,918 | 5/1988 | Wassenberg, II . |
| 4,775,636 | 10/1988 | Moeremans et al. .................... 436/518 |
| 4,948,481 | 8/1990 | Müllner . |

FOREIGN PATENT DOCUMENTS

| | | |
|---|---|---|
| 0361062 | 8/1989 | European Pat. Off. . |
| 0380313 | 1/1990 | European Pat. Off. . |

OTHER PUBLICATIONS

A. T. Andrews, Electrophoresis: Theory, techniques, and Biochemical and Clinical Applications 2nd Ed., Clarendon Press–Oxford, 1986.

*Primary Examiner*—Kathryn L. Gorgos
*Assistant Examiner*—Alex Noguerda
*Attorney, Agent, or Firm*—Denton L. Anderson; David A. Farah; Sheldon & Mak, Inc.

[57] ABSTRACT

A process for electroelution of a gel containing charged macromolecules, such as proteins or polynucleotides, comprising the steps of providing a plurality of adjacent parallel chambers having a trapezoidal cross-section, placing a gel containing the charged macromolecules onto first open sides of the chambers, placing a semipermeable membrane onto second open sides of the chambers, filling the chambers with an elution buffer and applying a voltage difference across the chambers so that charged macromolecules in the gel migrate into the elution buffers in the chambers. Also, an apparatus for electroelution of a gel containing charged macromolecules having, preferably, a plurality of adjacent parallel chambers having a trapezoidal cross-section and vents for removing the product without disassembling the apparatus.

53 Claims, 8 Drawing Sheets

APPARATUS AND PROCESS FOR ELECTROELUTION OF A GEL CONTAINING CHARGED MACROMOLECULES

This application is a 371 of PCT/DK92/00058 filed Feb. 25, 1992.

FIELD OF THE INVENTION

The present invention concerns a process and apparatus for electroelution of a gel containing charged macromolecules, such as proteins or DNA/RNA.

BACKGROUND

Electrophoresis of proteins or DNA/RNA in gels is widely used to separate compounds which differ in size and/or charge. Such compounds exhibit different migration distances and can be investigated by staining the gel or by transfer to a membrane suited for the study of antibody-antigen or other affinity interactions. Recovery of individual protein bands, however, is a laborious and time consuming procedure which generally has been based on cutting the gel into segments containing a single band, followed by homogenizing and elution, either by electroelution or by simple diffusion. Such a process is often ineffective and yields very high dilutions.

U.S. Pat. No. 3,956,099 discloses a complex system suited for continuous operations. The system separates components into separate compartments during the electrophoretic run. The procedure is not based on the elution of macromolecules already separated in a conventional gel, but includes instead a separating unit suited for large scale purification of proteins.

The processes and components described in U.S. Pat. Nos. 4,049,534, 4,725,348 and 4,747,918 all suited for electroelution of small gel fragments containing single components. The procedures include a preceeding localization and excision of the desired molecule, a technique which is time consuming and involves problems with respect to accuracy. These methods are therefore not suited for the simultaneous investigation of all components separated in a gel.

EP Published Application No. 0 380 313 discloses a field inversion electroblotting and elution device specially suited for transfer of high molecular mass compounds. The procedure includes a preceeding identification of the band of interest and, therefore, has the same limitations as mentioned in relation to the methods described in the above-mentioned U.S. Pat. Nos. 4,049,534, 4,725,348 and 4,747,918.

U.S. Pat. No. 4,181,594 discloses a matrix recovery apparatus wherein compounds contained in a slab gel are electroeluted directly upwards into multiple wells. Each compound is eluted into several wells separated by walls of a considerable thickness.

The Blotelutor® apparatus (manufactured by Biometra, Göttingen, Germany) provides a unit which is exclusively suited for the elution of proteins from two-dimensional gels. The proteins are eluted into wells separated by walls of a considerable thickness. Further, the method underlying this apparatus is not based on a physiological buffer and does not include a pre-equilibration step to ensure a fixed positioning of the gel during elution.

None of these prior systems meet the need for conventional, simultaneous elution of all compounds separated in a one-dimensional gel. A system with these features would greatly facilitate the biological and chemical screening procedure of complex protein or polynucleotide mixtures.

SUMMARY

It is an object of the present invention to provide a process for simultaneous elution of separated charged macromolecules such as DNA/RNA contained in a one dimensional gel, and to provide an apparatus and method of use in carrying out the process. According to the process of the invention, a simultaneous elution of a mixture the separated charged macromolecules, such as proteins, in an entire gel, such as a polyacrylamide or agarose gel, is performed. The charged molecules are, thus, divided into narrow fractions each containing single or closely located compounds, and the greater part of ione detergents, such as sodium dodecyl sulphate (SDS), as is removed.

The novelty according to the process of the invention is the collective elution of an entire gel. The present invention additionally provides an electroelution unit suited for the simultaneous elution of all compounds separated in a whole gel by the process of the invention. The unit very efficiently elutes ordinary gels (0.5–1 mm thick), but is also suitable for the elution of very thick gels (3–4 mm).

The process and the apparatus according to the present inventions is explained more fully with reference to the figures where:

DESCRIPTION

Figure 1A:
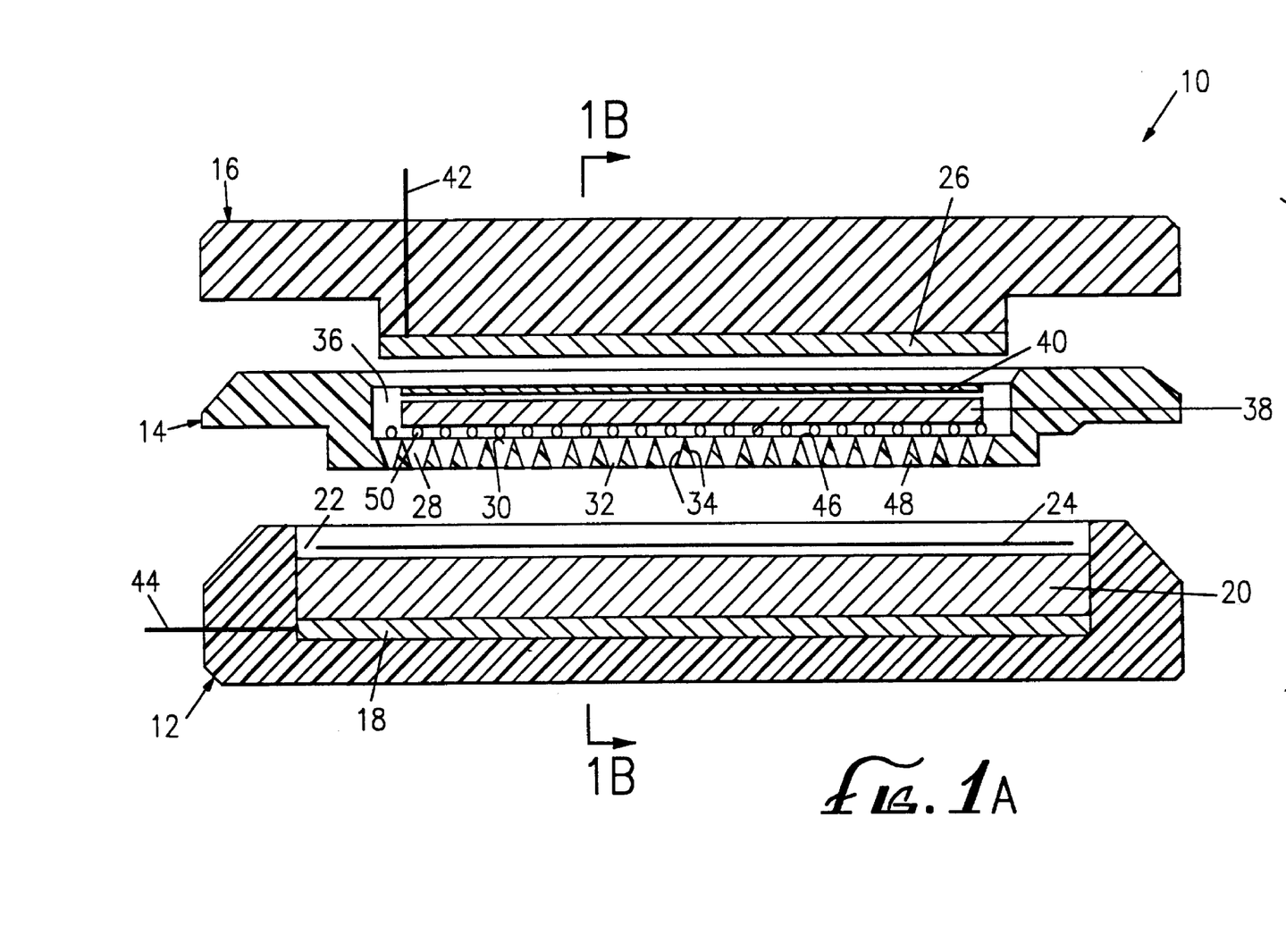
FIG. 1A is a schematic view of a multichamber electroelution apparatus according to the invention.
Figure 1B:
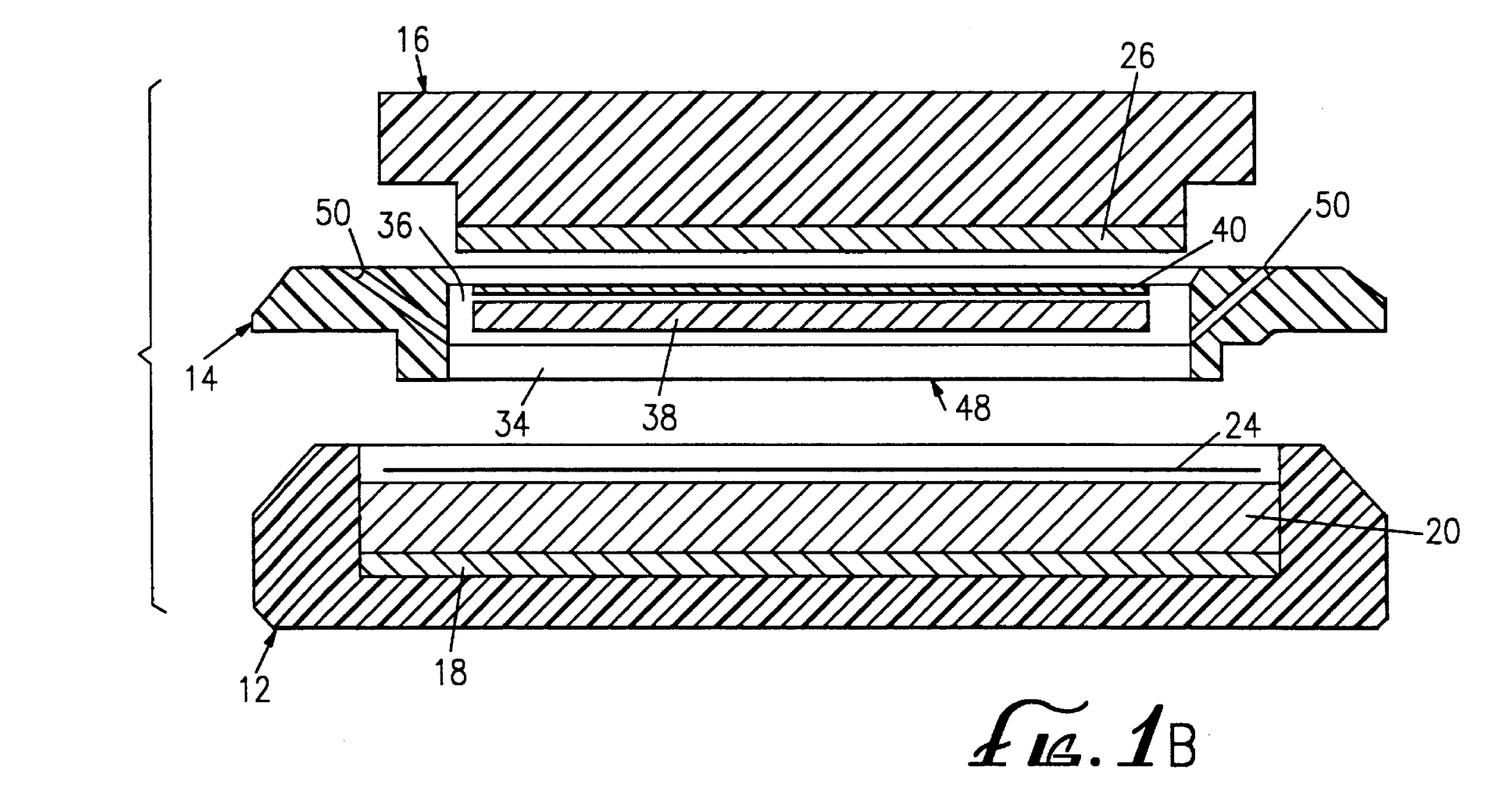
FIG. 1B is a cross-sectional view of the electroelution apparatus shown in FIGS. 1A and 1C, taken along the line of B—B.
Figure 1C:
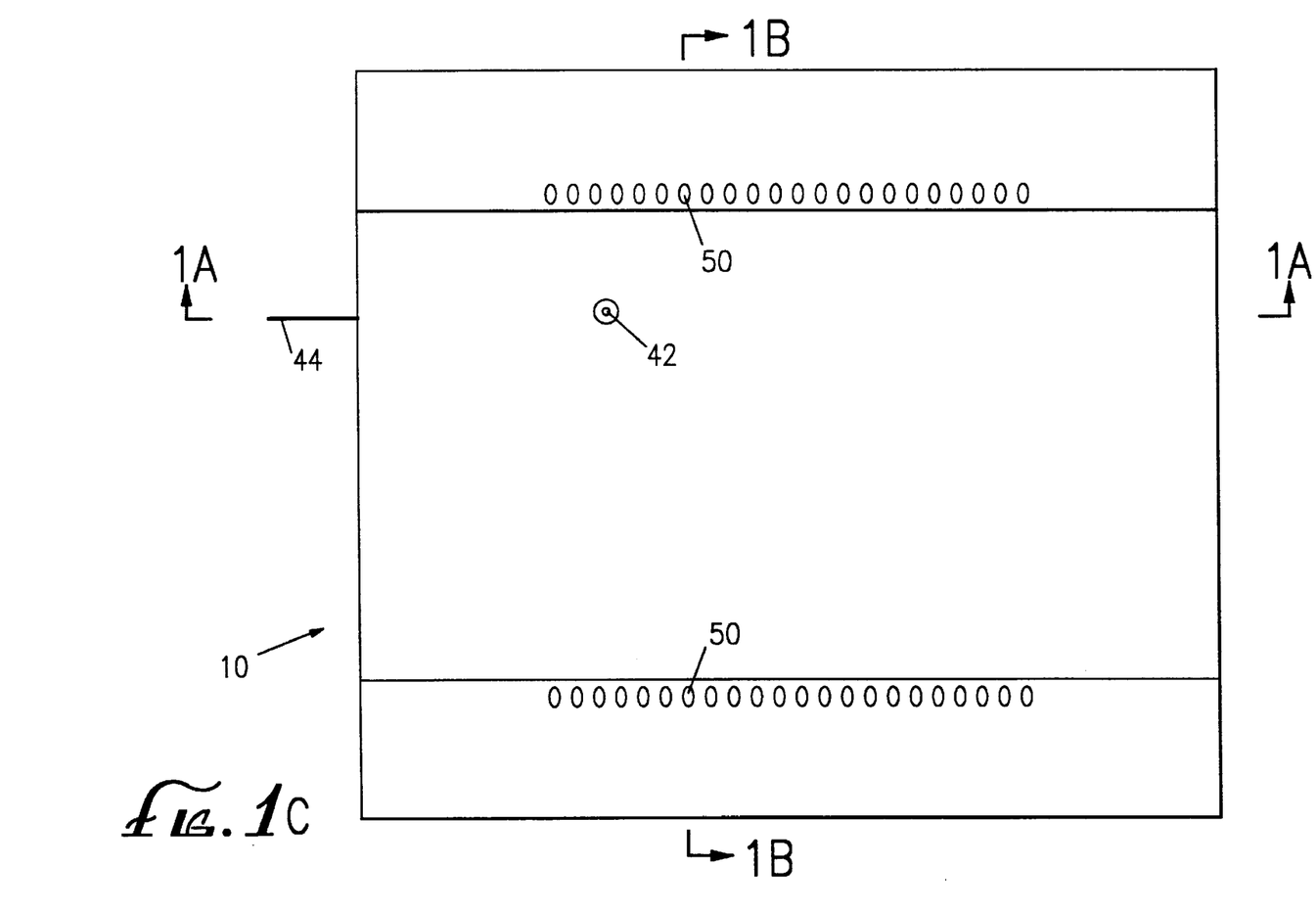
FIG. 1C is a top plan view of the electroelution apparatus shown in FIGS. 1A and 1B.

Referring now to FIG. 1A, there is shown a schematic view of a multichamber electroelution apparatus 10 according to the present invention. FIG. 1B is a cross-sectional view of the electroelution apparatus 10, taken along the line B—B. FIG. 1C is a top plan view of the electroelution apparatus 10 shown in FIGS. 1A and 1B a detergent resistant plastic material.

The base 12 of the apparatus 10 contains a graphite anode (18) and a sponge (20) filled with buffer. In the base 12 is located a reservoir 22 which receives excess buffer generated as the sponge 20 is compressed during mounting of the frame (14). A sheet of a-semipermeable membrane 24, such as a dialysis membrane, is placed on top of the sponge 20, and the frame is tightly connected to the base 12 by means of finger screws not shown. Optionally the membrane 24 may be fixed to the sponge 20, e.g. by glueing. A graphite cathode (26) is built into a safety cover (16).

The frame 14 contains multiple parallel chambers (28) of a trapezoidal shape, having a top 30, an opposing bottom 32, which is shorter than the top, and opposing first and second sides 34. When the apparatus 10 is assembled, the bottom 32 is closed downwards by the close surface to surface contact with the membrane (24). The volume of each chamber 28 is less than 15 ml, preferably about 3 ml.

The frame 14 contains an indentation 36 in which a gel (38) is placed. A sheet of filter paper (40) wetted with buffer is preferably placed between the gel (38) and the graphite cathode (26).

Figure 1D:
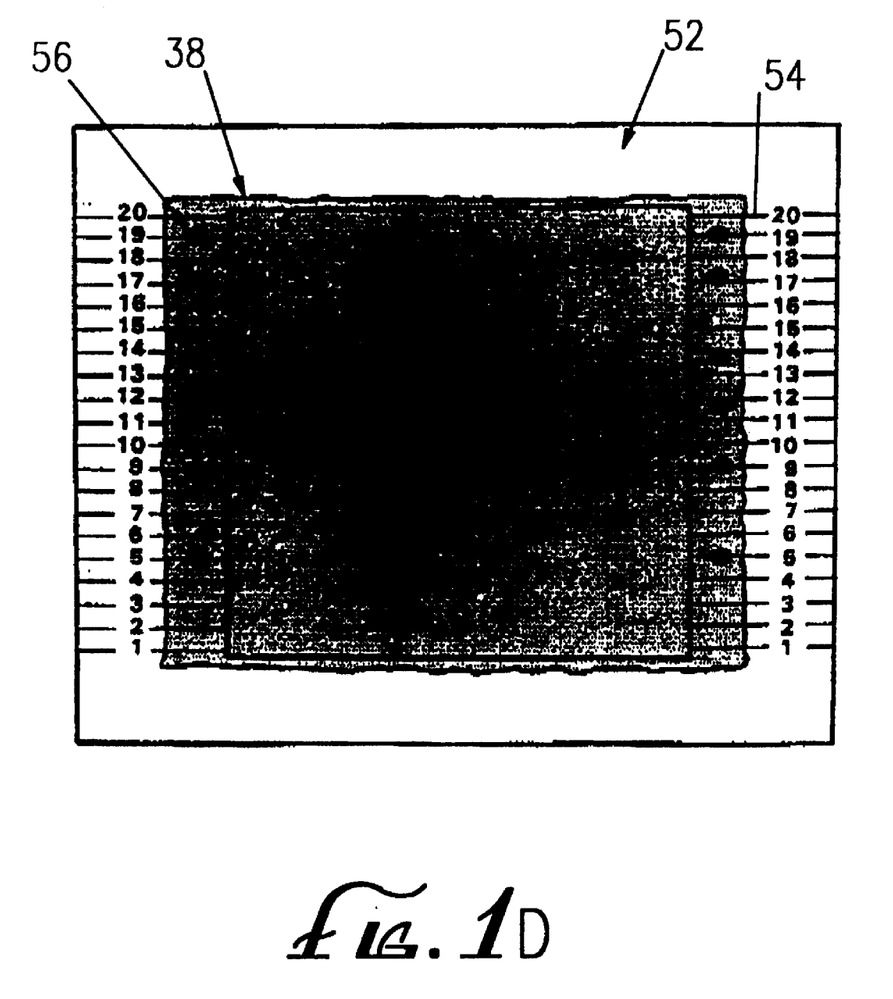
FIG. 1D is a top view of a template for use with the apparatus according to the invention.

Referring now to FIG. 1D, there is shown a template 52 for use in precisely trimming the gel 38 according to the size of the indentation 36. The template 52 is made of clear acrylic plastic and each chamber 28 is indicated. The template 52 is furthermore equipped with adjustment lines 54 which are used to orientate the template 52 before excision of the gel.

A voltage potential of about 40 volts is provided, and the power supply not shown should be adjustable to provide such a voltage. The power supply is connected to the cathode (26) and the anode (18) by means of cables (42 and 44, respectively. Optionally, the power supply can be built into the safety cover (16).

According to an embodiment of the present invention, there is provided a method for electroelution of a gel. The necessary period for complete elution is generally between 8 and 15 minutes for a 0.75 mm gel. After elution the current is reversed for 10 seconds to loosen material sticking to the membrane 24. The product obtained is harvested by a plastic pipette through the side vents 50 on the apparatus 10.

To start the electroelution process the gel 38 containing the separated molecules is pre-equilibrated in a buffer, preferably for about 30–40 minutes. A preferred buffer, if the products are to be used in cellular assays, is a physiological buffer of low ionic strength, preferably a 2 mM phosphate buffer (pH=6.5). During equilibration the gel 38 will swell and obtain its final size, thereby ensuring a fixed positioning of the gel 38 in the frame 14 during elution. The buffer is changed three times to ensure the removal of excess salt and ionic detergents from the gel 38. The gel 38 is removed from the buffer and placed on a clean glass plate, and then the part which is to be eluted is excised with the aid of the template 52. In the preferred use, gels are run with pre-stained molecular weight markers 56 in the peripheral lanes. By aiming the template adjustment lines 59 towards the markers 56 a precise orientation and reproducible excision of the gel 38 can be obtained. This method guarantees the important parallel course of gel bands and elution chambers 28.

The sponge 20 in the base of the apparatus 10 is filled with buffer. A dialysis membrane 24 soaked in the buffer is placed on top of the sponge 20 and the frame 14 is mounted by means of the finger screws not shown. The sponge 20 functions as a support for the membrane 24 and its compression ensures a tight closing of each chamber. The chambers are filled with buffer and the template is used to assist transfer the gel 38 to the indentation 36 of the frame 14. Two sheets of thick filter paper 40, adjusted to the size of the gel 38 are soaked in buffer and placed on top of the gel 38. The graphite cathode 26 is mounted and a voltage potential of preferentially about 40 volts is provided.

During the elution charged molecules will migrate from the gel 38 into the buffer contained in the chambers 28. The upper part 46 of the walls 48 separating the chambers 28 are sharply pointed to minimize any area of suboptimal transfer. Ionic detergents (SDS) will migrate towards the anode 18 through the dialysis membrane 24, allowing the detergents to be effectively removed in the buffer.

The period necessary for complete elution depends on the compounds under investigation and the gel matrix used, but is preferably between 8 and 16 minutes. The elution is followed by reversal of the current for a short period of time, preferentially about 10 seconds, to loosen molecules sticking to the membrane. After elution the product is recovered by aspirating with a pipette through the vents 50 on the side of the frame 14. After harvesting of the product, the apparatus 10 is disassembled and the gel 38 is stained for protein/DNA to check whether the transfer was complete. Before the product is used in cellular assays all fractions are made isotonic by addition of a sufficient volume of 10×PBS.

According to another embodiment of the present invention there is provided a method of using the apparatus 10 for simultaneous electroelution and electroblotting. In accordance with this embodiment a sheet of suitable membrane is inserted in one side of the apparatus 10, thereby covering a variable part of all chambers 28. In this way molecules can be transferred into solution and simultaneously blotted onto the membrane. In a preferred embodiment T cell reactivity and antibody response towards separated protein mixtures can be investigated simultaneoulsy in a simple and accurate way.

In accordance with another embodiment of the present invention, there is provided a method for purification of single compounds in a simple and quick way. This method comprises the steps of removing a narrow strip of gel or electroblotted membrane containing the separated material, and localizing the compounds of interest by staining or by reaction with specific probes, which in a preferred embodiment are monoclonal antibodies. Each elution chamber 28 is indicated on the membrane by impressions from the upper part 46 of the walls 48. If a gel strip is stained, a number of 2–3 mm holes are punched to indicate the localization of the elution chambers 28. A precise punching is easily done by the aid of the template which carries a precise marking for each elution chamber 28. These reference strips enable a precise identification of the chamber which contains the relevant compound.

Figure 2:
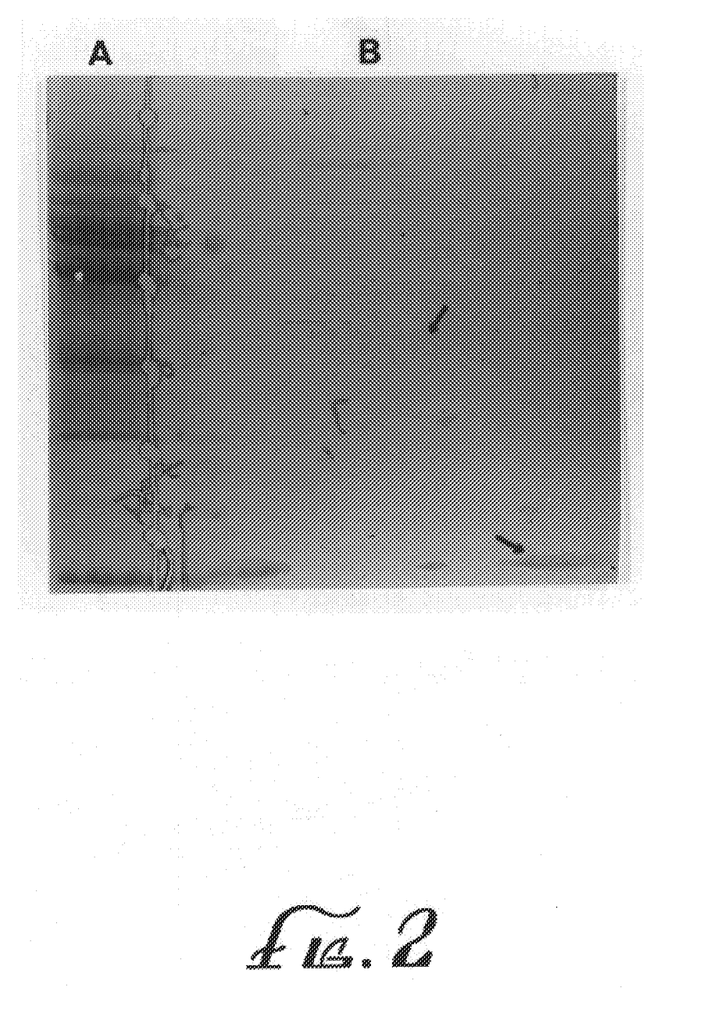
FIG. 2 is a photograph of a gel eluted in an apparatus as shown in FIG. 1 by means of a process according to the invention.

Referring now to FIG. 2, there is shown a photograph of a gel eluted in an apparatus according to the present invention by a process according to the present invention. As can be seen, the apparatus and process the present invention provide effective elution of all parts of a gel. The gel is divided into two areas, A and B.

Part A of the gel was removed before elution and stained for Part B, the eluted gel was stained for protein after termination of the elution process to evaluate if the transfer was complete.

As can be seen, the gel exhibits thin, faint lines (upper arrow) indicating the location of chamber wall edges, and two blurred areas bottom arrow in the bottom of the gel. These findings emphasize two important aspects of the present invention. First, the sharply pointed chamber walls minimize the areas of suboptimal transfer. Secondly, air air bubbles (lower arrow) underneath the gel will interfere with the protein transfer.

Figure 3:
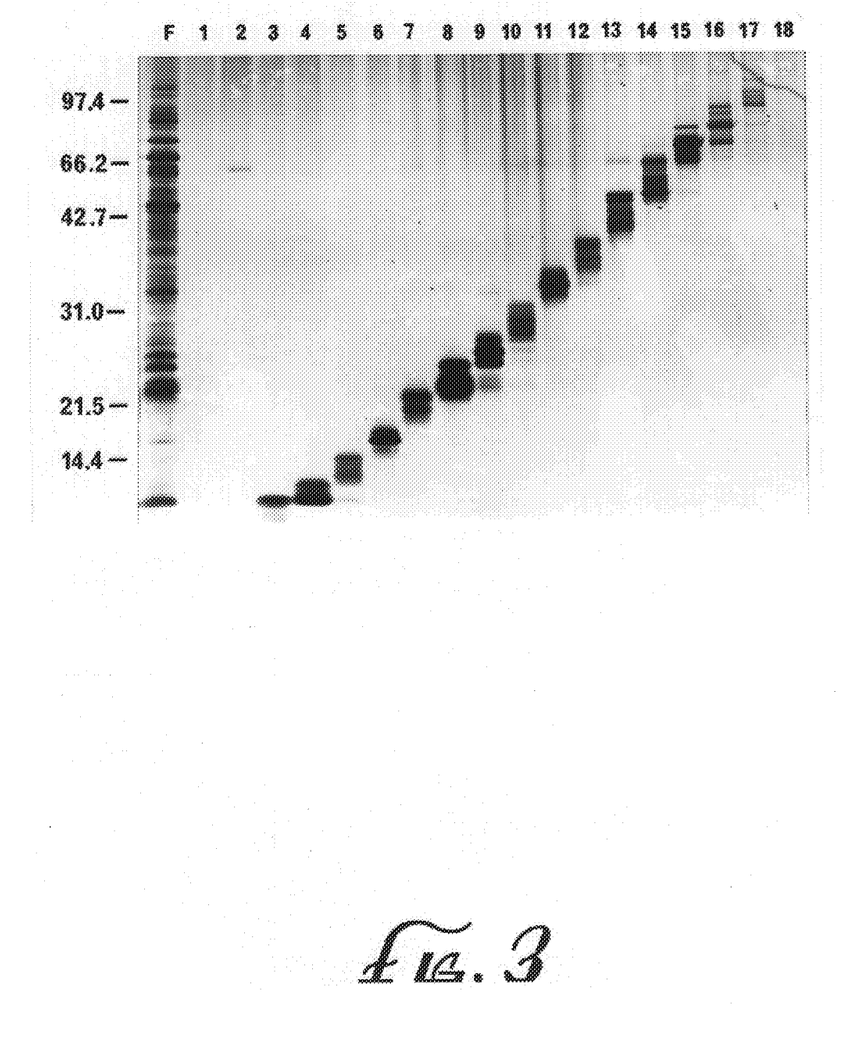
FIG. 3 is a photograph showing the fractionation of a complex mixture of proteins by means of the electroelution apparatus shown in FIG. 1.
Figure 4:
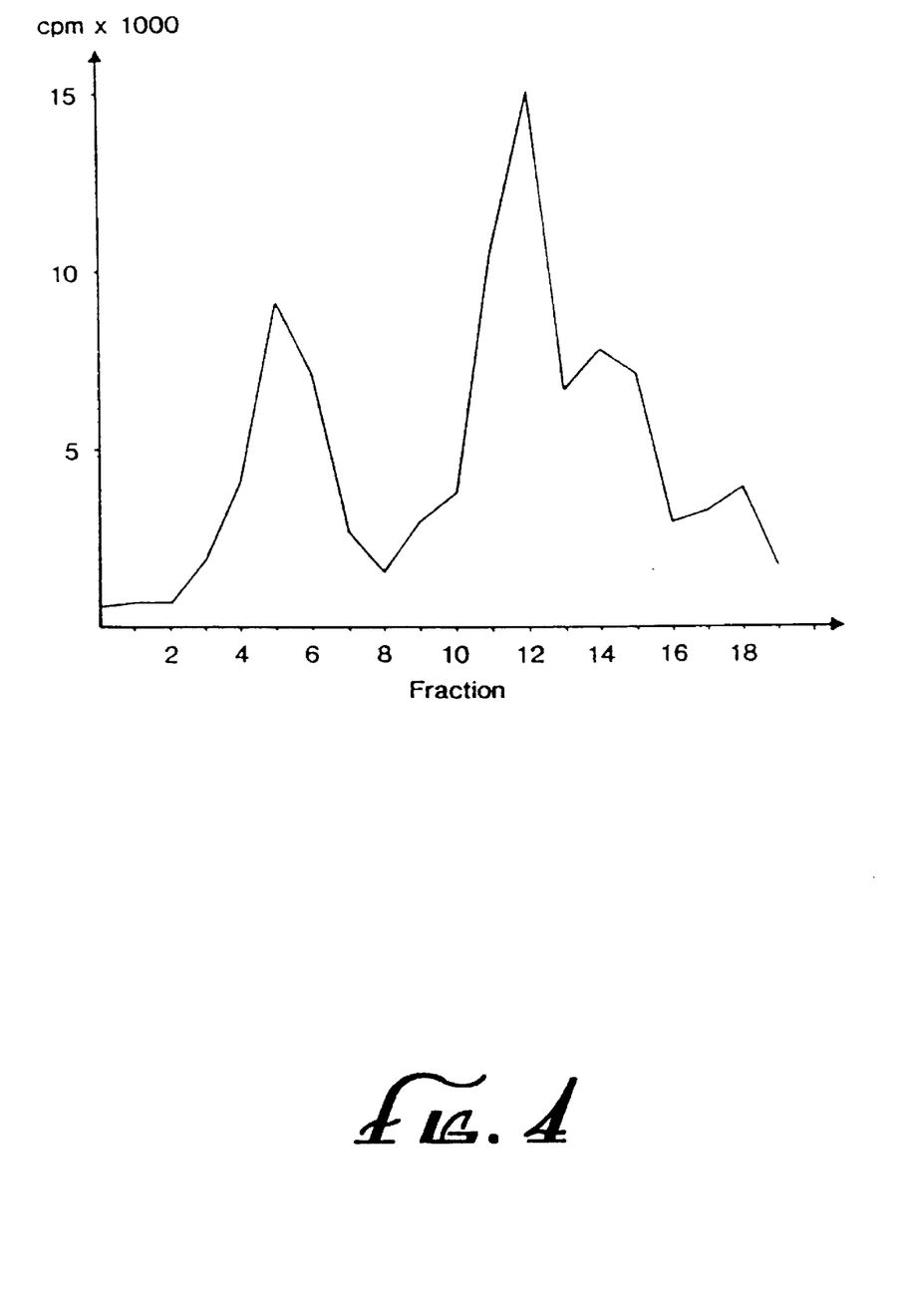
FIG. 4 is a graphic representation showing the cellular responses to fractions from the multichamber electroelutor of the present invention.
Figure 5:
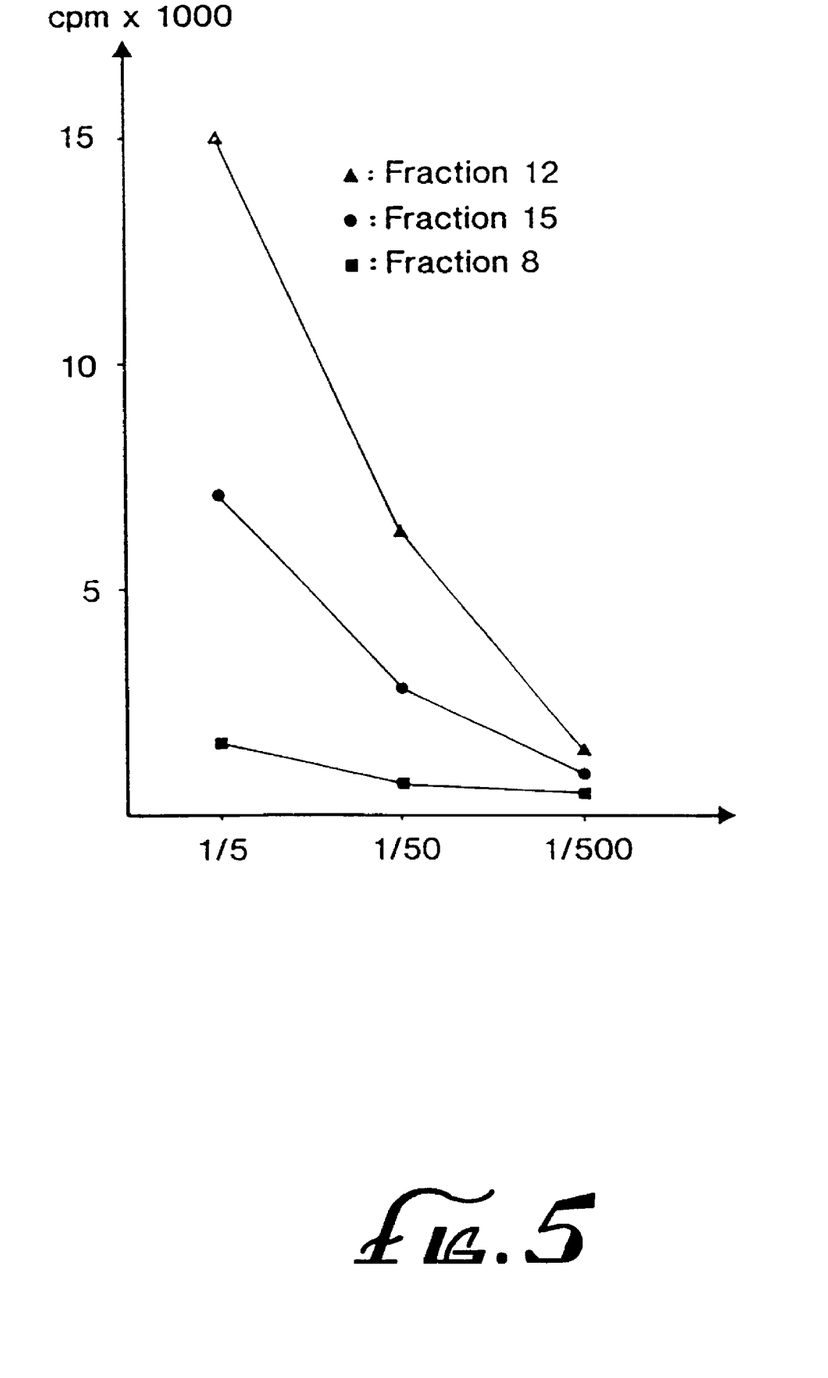
FIG. 5 is a graphic representation demonstrating that fractions from the multichamber electroelution apparatus are non-toxic.

Referring now to FIG. 3, there is shown a photograph of the fractionation of a complex mixture of proteins by the apparatus and method according to the present invention.

*Mycopacterium tuberculosis* culture filtrate was separated in 10–20% SDS-PAGE and fractionated with the multichamber electroelution apparatus of the present invention. The filtrate and the obtained fractions were analyzed by SDS-PAGE and silver staining.

Lane F shows the *Mycobacterium tuberculosis* filtrate prior to elution. Lanes 1–18 show the eluted fractions.

FIG. 4 shows the proliferative responses of spleen lymphocytes obtained from mice infected with *M. tuberculosis*. The cells were grown in cultures stimulated with fractions of *M. tuberculosis* culture filtrate in a dilution of 1:5. The proliferative response obtained with intact filtrate was 18600 cpm and the response of unstimulated cells was 500 cpm. The proliferation was measured by liquid scintillation counting of $^{3}H$ thymidine incorporation in the DNA of proliferative cells.

Referring now to FIG. 5, there is a graphic representation showing that the fractions from the multichamber electroelution apparatus according to the present invention, appear to be non-toxic. Low, medium and high stimulatory fractions from the multichamber electroelution apparatus were investigated in dilutions ranging from 1:5 to 1:500. All fractions exhibited a positive dose-response relationship, i.e. the higher dose gave a higher proliferative response. These results emphasize the non-toxic character of products from the electroelution apparatus.

As it appears from the afore-mentioned, the process and the apparatus according to the present invention provide several great advantages:

First, they provide a quick and simple way to obtain a simultaneous elution of all components separated in a one-dimensional gel of the type which is commonly used. Moreover, one-dimensional gels of varying thickness can be used with the process and apparatus ensuring maximum flexibility of the invention. The electroelution apparatus can therefore be used a part of routine protein purification procedures and the yields can be quantitatively and qualitatively analyzed.

The trapezoidal shaped wells provide for an even transfer of all protein bands.

Stretching of the frame 14 against the sponge 20 makes the assembled apparatus 10 an efficient and easy to handle package.

The buffer is non-toxic and free of chloride ions which might otherwise cause problems during the elution. The same buffer is used in all parts of the electroelution apparatus, thereby saving labor.

When the elution is completed, the product can be removed from the apparatus 10 through side vents 50 without disassembling the apparatus 10. This ensures a high degree of purity of the product. The product is completely non-toxic and, therefore, suited for a number of different uses.

Finally, using the template 52 ensures an accurate and reproducible fractionation.

I claim:

1. A process for electroelution of a gel containing charged macromolecules, comprising the steps of:

(a) providing an apparatus having a plurality of adjacent parallel chambers, each chamber having a trapezoidal cross-section and comprising a top and an opposing bottom, and a first closed side and an opposing second closed side, wherein the top is longer than the bottom;

(b) placing a semipermeable membrane adjacent the bottoms of the chambers;

(c) filling the chambers with an elution buffer; and (d) placing a gel containing charged macromolecules across the tops of the chambers;

(e) applying a voltage difference across the chambers for a period of time sufficient for the charged macromolecules in the gel to migrate into the elution buffers in the chambers.

2. The process of claim 1, wherein the buffer in the filling step is a phosphate buffer.

3. The process of claim 2, wherein the buffer is present in an amount of about 2 mM.

4. The process of claim 1, wherein, in the providing step, the first closed side of a chamber forms a triangle with the second closed side of an adjacent chamber.

5. The process of claim 4, wherein the triangle forms a pointed tip adjacent the gel in the placing step.

6. The process of claim 1, wherein, in the placing step, the charged macromolecules in the gel are in bands and the gel is placed such that the bands are parallel with the chambers.

7. The process of claim 1, wherein the elution buffer in the filling step contains ionic detergents and wherein the period of time in the applying step is sufficient to cause substantially all of the ionic detergents present in the elution buffer to pass through the semipermeable membrane into the sponge.

8. The process of claim 1, wherein the period of time in the applying step is between about 8 and 16 minutes.

9. The process of claim 1, further comprising a step of reversing the voltage difference for a period of time after the applying step.

10. The process of claim 9, wherein the period of time that the voltage difference is reversed in the reversing step is about 10 seconds.

11. The process of claim 1, wherein the elution buffer in the filling step has a low ionic strength.

12. The process of claim 1 for simultaneous electroelution and electroblotting of separated charged macromolecules, wherein a variable part of all chambers are covered with a suitable membrane for blotting of the molecules thereon.

13. An electroelution apparatus for eluting charged macromolecules in a gel comprising:

(a) a base with an anode, the base containing a sponge covered by a semipermeable membrane;

(b) a frame containing multiple parallel chambers, wherein each chamber has an open bottom; and (c) a safety cover with a cathode;

wherein the base is configured such that the semipermeable membrane closes the open bottom of the chambers when the frame is set into the base.

14. The apparatus of claim 13, wherein the chambers have trapezoidal cross-sections.

15. The apparatus of claim 14, wherein each chamber has a top opposing the bottom, and a first side and a second side opposing the first side, and wherein the top is longer than the bottom.

16. The apparatus of claim 15, wherein the first side of a chamber forms a triangle with the first side of an adjacent chamber.

17. The apparatus of claim 16, wherein the triangle forms a pointed tip adjacent the tops of the chambers.

18. The apparatus of claim 13, wherein the semipermeable membrane is permeable to ionic detergents, allowing passage of the ionic detergents into the sponge, but substantially impermeable to the charged macromolecules.

19. The apparatus of claim 13, wherein the safety cover further includes an integral power supply.

20. The apparatus of claim 13, further comprising side vents for recovering the eluted macromolecules without disassembling the apparatus.

21. The apparatus of claim 13, further comprising a membrane for simultaneous elution and blotting.

22. The apparatus of claim 13, wherein the anode comprises graphite.

23. The apparatus of claim 13, wherein the anode is integral with the base.

24. The apparatus of claim 13, wherein the cathode comprises graphite.

25. The apparatus of claim 13, wherein the cathode is integral with the safety cover.

26. The apparatus of claim 13, wherein the sponge contains a buffer.

27. The apparatus of claim 13, wherein the semipermeable membrane is fixed to the sponge.

28. The apparatus of claim 13, further comprising a template to assist in excision of the gel before electroelution.

29. The apparatus of claim 28, wherein the charged macromolecules in the gel are in bands, and the template is provided with adjustment lines to orient the bands with respect to the chambers such that migration of the macromolecules occurs in a parallel course to the chambers.

30. A template for use in the apparatus of claim 28, wherein the template comprises a marking indicating the position of each chamber in order to identify a chamber containing a single species of molecule of the charged macromolecules.

31. A process for electroelution of a gel containing charged macromolecules, comprising the steps of:
   (a) providing an apparatus according to claim 13;
   (b) placing a gel containing charged macromolecules in the frame;
   (c) applying a voltage difference across the chambers for a period of time sufficient for the charged macromolecules in the gel to migrate into the chambers.

32. An electroelution apparatus for eluting charged macromolecules in a gel comprising:
   (a) a base including a sponge covered by a semipermeable membrane;
   (b) a frame containing multiple parallel chambers, wherein each chamber has a bottom; and
   (c) side vents in the frame to harvest the isolated compounds without disassembling the apparatus.

33. The apparatus according to claim 32, wherein the base is configured such that the semipermeable membrane closes the bottom of the chambers when the frame is set into the base.

34. The apparatus according to claim 32, further comprising a safety cover with a cathode therein.

35. The apparatus according to claim 32, further comprising a template for the precise excision of the gel before electroelution.

36. The apparatus of claim 32, wherein the chambers have trapezoidal cross-sections.

37. The apparatus of claim 32, wherein the semipermeable membrane allows the passage of salts and ionic detergents into the sponge.

38. The apparatus of claim 32, wherein the semipermeable membrane is permeable to ionic detergents, allowing passage of the ionic detergents into the sponge, but substantially impermeable to the charged macromolecules.

39. The apparatus of claim 32, further comprising a template to assist in excision of the gel before electroelution.

40. The apparatus of claim 39, wherein the charged macromolecules in the gel are in bands, and wherein the template is provided with adjustment lines to orient the bands with respect to the chambers such that migration of the macromolecules occurs in a parallel course to the chambers.

41. The apparatus of claim 39, wherein the template comprises an indication of each chamber in order to identify a chamber containing a single species of molecule of the charged macromolecules.

42. The apparatus of claim 32, further comprising a membrane for simultaneous elution and blotting.

43. The apparatus of claim 32, wherein the base further comprises an anode.

44. The apparatus of claim 43, wherein the anode comprises graphite.

45. The apparatus of claim 43, wherein the anode is integral with the base.

46. The apparatus of claim 32, additionally comprising a safety cover with a cathode.

47. The apparatus of claim 46, wherein the cathode comprises graphite.

48. The apparatus of claim 46, wherein the cathode is integral with the safety cover.

49. The apparatus of claim 32, wherein the semipermeable membrane is fixed to the sponge.

50. The apparatus of claim 32, wherein each chamber has a top opposing the bottom, and a first side and a second side opposing the first side, and wherein the top is longer than the bottom.

51. The apparatus of claim 50, wherein the first side of a chamber forms a triangle with the first side of an adjacent chamber.

52. The apparatus of claim 50, wherein the triangle forms a pointed tip adjacent the tops of the chambers.

53. A process for electroelution of a gel containing charged macromolecules, comprising the steps of:
   (a) providing an apparatus according to claim 32;
   (b) placing a gel containing charged macromolecules in the frame;
   (c) applying a voltage difference the across the chambers for a period of time sufficient for the charged macromolecules in the gel to migrate into the chambers.

* * * * *

UNITED STATES PATENT AND TRADEMARK OFFICE
CERTIFICATE OF CORRECTION

PATENT NO : 5,840,169
DATED : November 24, 1998
INVENTOR(S): Peter Andersen

It is certified that error appears in the above-identified patent and that said Letters Patent is hereby corrected as shown below:

Cover Page at column 1, lines 9-11:
delete the following text in its entirety "[*] Notice: The portion of the term of this patent subsequent to Aug. 13, 2011, has been disclaimed.".

Cover Page at column 2, line 2:
replace "[45] Date of Patent: *Nov. 24, 1998" with
--[45] Date of Patent: Nov. 24, 1998--.

Signed and Sealed this

Fourth Day of May, 1999

Attest:

Q. TODD DICKINSON

Attesting Officer

Acting Commissioner of Patents and Trademarks